United States Patent
Wagshul

(10) Patent No.: US 10,694,973 B2
(45) Date of Patent: Jun. 30, 2020

(54) PISTON DEVICE FOR MAGNETIC RESONANCE ELASTOGRAPHY AND USES THEREOF

(71) Applicant: Albert Einstein College of Medicine, Bronx, NY (US)

(72) Inventor: Mark Elliott Wagshul, Stamford, CT (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 1014 days.

(21) Appl. No.: 15/086,163

(22) Filed: Mar. 31, 2016

(65) Prior Publication Data

US 2016/0287130 A1    Oct. 6, 2016

Related U.S. Application Data

(60) Provisional application No. 62/143,265, filed on Apr. 6, 2015.

(51) Int. Cl.
*A61B 5/055*  (2006.01)
*G01R 33/563*  (2006.01)
*A61B 5/00*  (2006.01)

(52) U.S. Cl.
CPC .......... *A61B 5/055* (2013.01); *A61B 5/0051* (2013.01); *A61B 5/4088* (2013.01); *A61B 5/4094* (2013.01); *G01R 33/56358* (2013.01); *A61B 5/0042* (2013.01); *A61B 5/4064* (2013.01); *A61B 5/4244* (2013.01); *A61B 5/4504* (2013.01); *A61B 5/4514* (2013.01)

(58) Field of Classification Search
None
See application file for complete search history.

(56) References Cited

U.S. PATENT DOCUMENTS

2010/0045289 A1*  2/2010  Chopra ................ G01R 33/28
                                                         324/307

OTHER PUBLICATIONS

Uffmann et al. ,"Actuation Systems for MR elastography", IEEE Eng. Med. And Bio. Magazine, 2008.*
Tse, Z T H et al., entitled "Piezoelectric actuator design for MR elastography: implementation and vibration issues," The International Journal of Medical Robotics and Computer Assisted Surgery, 2011; 7:353-360.

* cited by examiner

*Primary Examiner* — Carolyn A Pehlke
*Assistant Examiner* — Marjan Saboktakin
(74) *Attorney, Agent, or Firm* — Foley & Hoag LLP; Erik A. Huestis

(57) ABSTRACT

Disclosed are piston actuator devices and their uses for magnetic resonance elastography (MRE).

15 Claims, 5 Drawing Sheets

PISTON DEVICE FOR MAGNETIC RESONANCE ELASTOGRAPHY AND USES THEREOF

CROSS-REFERENCE TO RELATED APPLICATION

This application claims the benefit of U.S. Provisional Patent Application No. 62/143,265 filed Apr. 6, 2015, the contents of which are herein incorporated by reference in their entirety.

BACKGROUND OF THE INVENTION

Magnetic resonance elastography (MRE) is a technique that has been developed over the last 10-15 years for the noninvasive measurement of the mechanical properties of biological tissue, such as liver or brain. It is based on the fact that magnetic resonance imaging (MRI), while demonstrating relatively modest spatial resolution (at least compared to microscopy techniques, for example), can be made extremely sensitive to microscopic motion that is much smaller than the size of the pixels of the MRI image. This relies on the measurement of the "phase" of the MRI signal, which can be thought of as a measurement of the direction in which the atomic spins of the tissue are facing. By specifically sensitizing the MRI technique to microscopic motion, it is possible to detect tissue motion that is less than one micron in amplitude.

With the ability to measure extremely small amplitudes of tissue motion, it becomes possible to measure the mechanical properties of tissue with very small vibrations of the tissue. There are two types of vibration of tissue that are possible: compression and shear. Compression is produced by compressing or expanding the tissue, and shear is produced by pulling on the two sides of the tissue in opposite directions. Whereas applying a static force on the tissue will produce a static compression or shear, applying an oscillating force will cause compression or shear waves to propagate through the tissue. The propagation of these waves (e.g. the speed of the propagation, or amplitude of the wave) depends on the local mechanical properties of the tissue. Thus, by producing and detecting these compression or shear waves in the tissue, it is possible to measure the mechanical properties of the tissue (i.e., by solving the equations of motion of the tissue). While it is possible to do this with either compression or shear waves, the propagation speed of compression waves is much faster and typically too fast to measure, given the speed limitations of MRI. Thus, typical MRE relies on the production and detection of shear waves, and measurement of the shear mechanical properties (e.g., the so-called shear modulus and shear viscosity).

In practice, this works as follows: the tissue is vibrated at a fixed frequency. If these vibrations are applied in the correct direction, this vibration of the tissue sets up shear waves that propagate through the tissue. The MRE sequence is then used to measure these waves, and then mathematical equations are used to back out the shear modulus and shear viscosity in every pixel of the image.

The present invention addresses the need for improved devices for MRE.

SUMMARY OF THE INVENTION

The present invention provides non-metallic magnetic resonance elastography (MRE) actuators comprising a non-metallic body having an open end and a closed end; a non-metallic piston disposed within the body, the piston having an end that protrudes from the open end of the body and an opposite end; a restorative device that connects the closed end of the body to the opposite end of the piston and that produces a restoring force on the piston when the piston is displaced relative to the body; a first non-metallic connector on the body that provides the body with a connection to an air, hydraulic or mechanical source of pressure that vibrates the piston; and a non-metallic interface located on the end of the piston that protrudes from the body, where the interface provides a contact area with a subject.

The invention also provides methods of producing a shear wave in a tissue for magnetic resonance elastography (MRE), the methods comprising applying the interface of any of the actuators described herein to skin overlying tissue to be imaged and vibrating the piston.

DETAILED DESCRIPTION OF THE INVENTION

Figure 1:
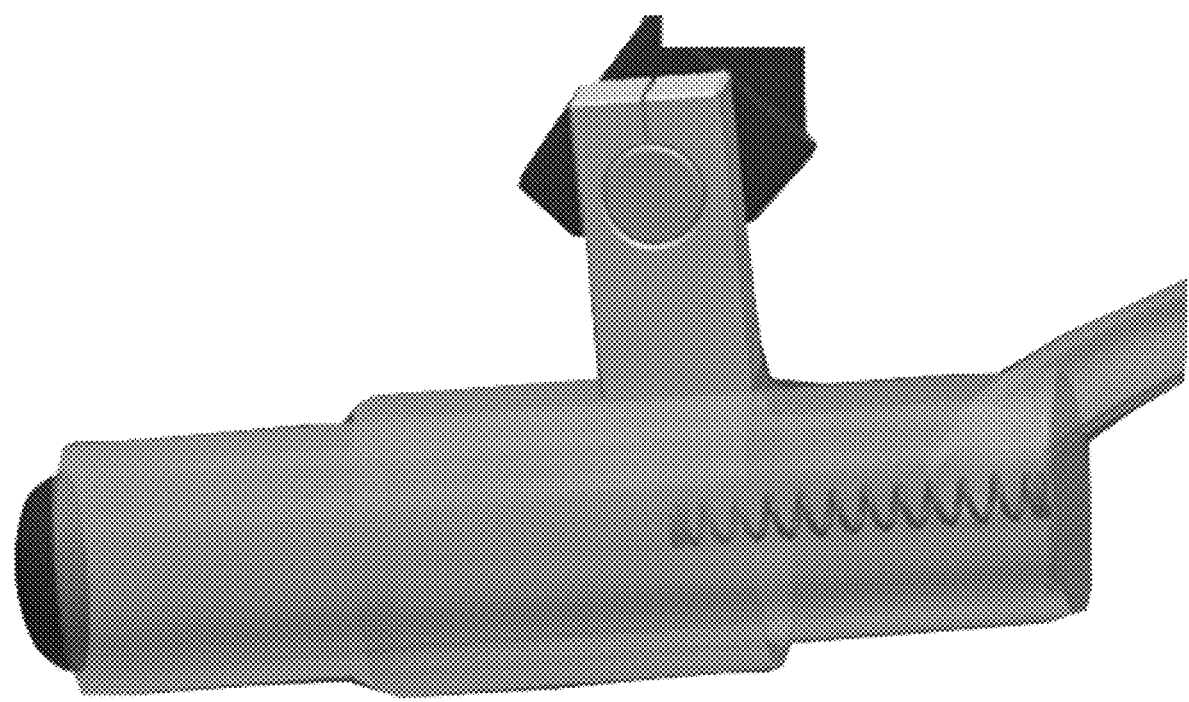
FIG. 1. Example of a magnetic resonance elastography (MRE) actuation device. Oscillatory air pressure is fed into the tube on the right, into the chamber behind the piston actuator, which then vibrates against the tissue of interest.

The present invention provides a non-metallic magnetic resonance elastography (MRE) actuator comprising
- a non-metallic body having an open end and a closed end;
- a non-metallic piston disposed within the body, the piston having an end that protrudes from the open end of the body and an opposite end;
- a restorative device that connects the closed end of the body to the opposite end of the piston and that produces a restoring force on the piston when the piston is displaced relative to the body;
- a first non-metallic connector on the body that provides the body with a connection to an air, hydraulic or mechanical source of pressure that vibrates the piston; and
- a non-metallic interface located on the end of the piston that protrudes from the body, where the interface provides a contact area with a subject. The actuator can further comprise a second non-metallic connector on the body that provides connection with a magnetic resonance imaging (MRI) device.

The restorative device can be, for example, a spring, or a foam or rubber restorative device.

Any suitable non-metallic material or materials can be used. Different components of the actuator can be made from the same or different materials. For example, any one or more of the body, piston, restorative device, first connector, interface and second connector can be made of plastic. The interface can comprise a soft surface that contacts the subject or tissue to be imaged. Suitable soft surface materials include, but are not limited to, rubber.

The piston can be acoustically coupled to a device that provides a vibratory signal to vibrate the piston.

The piston can vibrate at a frequency within a range, for example, of 20-200 Hz. The piston can vibrate, for example, with an amplitude of 10-350 microns, or 10-150 microns, or 100-150 microns.

The actuator can be dimensioned and configured for vibrating against bone, such as, for example, cheekbone, skull, pelvic bone or spinal veterbrae. The actuator can be dimensioned and configured for imaging, for example, the brain or cartilage in the arm or leg.

The actuator can be dimensioned and configured for vibrating against soft tissue, such as, for example, the abdomen. The actuator can be dimensioned and configured for imaging, for example, the liver or kidney.

The invention also provides a method of producing a shear wave in a tissue for magnetic resonance elastography (MRE), the method comprising applying the interface of any of the actuators disclosed herein to skin overlying the tissue to be imaged and vibrating the piston.

The actuator can be placed on skin overlying soft tissue, such as, for example, the abdomen, or the actuator can be placed on skin overlying bone, such as, for example, the cheekbone, skull, pelvic bone or spinal veterbrae.

In different embodiments, one actuator can be positioned on one side of a subject or tissue to be imaged and a second actuator can be positioned on an opposite side of the subject or tissue. The two actuators can be operated out of phase with each other. For example, one actuator can be positioned on skin overlying the left cheekbone and a second actuator can be positioned overlying the right cheekbone.

The shear wave that is produced in the tissue can have an amplitude, for example, of 10-20 microns. The actuator can produce, for example, 40-60 microns of brain motion. Vibrations can be applied to the tissue for, e.g., 1-15 minutes.

The methods can be used for diagnosis and/or prognosis of disease. The disease can be, for example, brain disease or liver disease. The disease can be, for example, cancer, hydrocephalus, Alzheimer's disease, epilepsy, multiple sclerosis, liver cirrhosis, or liver fibrosis.

This invention will be better understood from the Experimental Details, which follow. However, one skilled in the art will readily appreciate that the specifics discussed are merely illustrative of the invention as described more fully in the claims that follow thereafter.

Experimental Details

Introduction

What is important to understand for the current invention is that the larger the amplitude of the shear waves, the easier it is to detect the waves and the better the extraction of the shear properties (i.e., noise in the image will corrupt the shear property calculations leading to noise, and errors in the estimations of the shear properties). The calculations also rely on the fact that the vibrations are well characterized, i.e. that the frequency of the vibrations is well known and reproducible. From a practical standpoint, it is only possible to vibrate the tissue with a limited vibration amplitude before it become intolerable (or potential risky) for the subject.

All of the above descriptions dictate that the vibration of the tissue of interest be highly efficient, so that the shear wave amplitude is high with minimal discomfort to the subject, and have high fidelity so that the coupling of the vibrations to the subject are accurate (e.g. if the vibrating element (called an actuator) is moving at a particular frequency, the body part will vibrate only at that same frequency). If there is not a very tight coupling between the actuator and the body part, this last condition may not be met.

Most of the current actuators utilize a vibrating membrane that is placed against the tissue of interest and then coupled to a vibrating driver source. A currently available commercial device is designed for liver imaging. Unless the membrane is tightly coupled to the underlying tissue, the membrane can lift off of the tissue creating a "jack-hammer-like" effect, which is caused by the higher frequencies of the vibration—so-called higher harmonics.

Such designs are extremely inefficient for brain MRE. This is because the skull and the cerebrospinal fluid within the skull that bathes the brain minimize the effect of impact to the skull. This design of nature makes it difficult to efficiently vibrate the brain, since one cannot vibrate the brain directly, and the cerebrospinal fluid within the skull minimizes the transfer of vibrations from the skull to the brain. Thus, it is extremely critical in this case to efficiently vibrate the skull in order to produce as much brain vibration with as little as possible skull vibration (which obviously becomes uncomfortable for the subject as the size of the skull vibrations increase).

In addition, the fidelity of the reconstruction of MRE data critically depends on the assumption that the tissue of interest (e.g., brain) is vibrating at a single frequency. This is because the spatial pattern of the shear waves is dependent on frequency, and vibration at additional frequencies will therefore distort the shear wave pattern, subsequently leading to distortion of the elasticity maps produced from the MRE reconstruction. Thus, the efficiency of the actuator in producing high fidelity vibrations, i.e. exclusively at the primary frequency, is critical for reconstructing high quality elastance maps. As noted, this requires a tight coupling of the actuator to the tissue of interest, on which the current invention is based.

Description of the Invention

Figure 2:
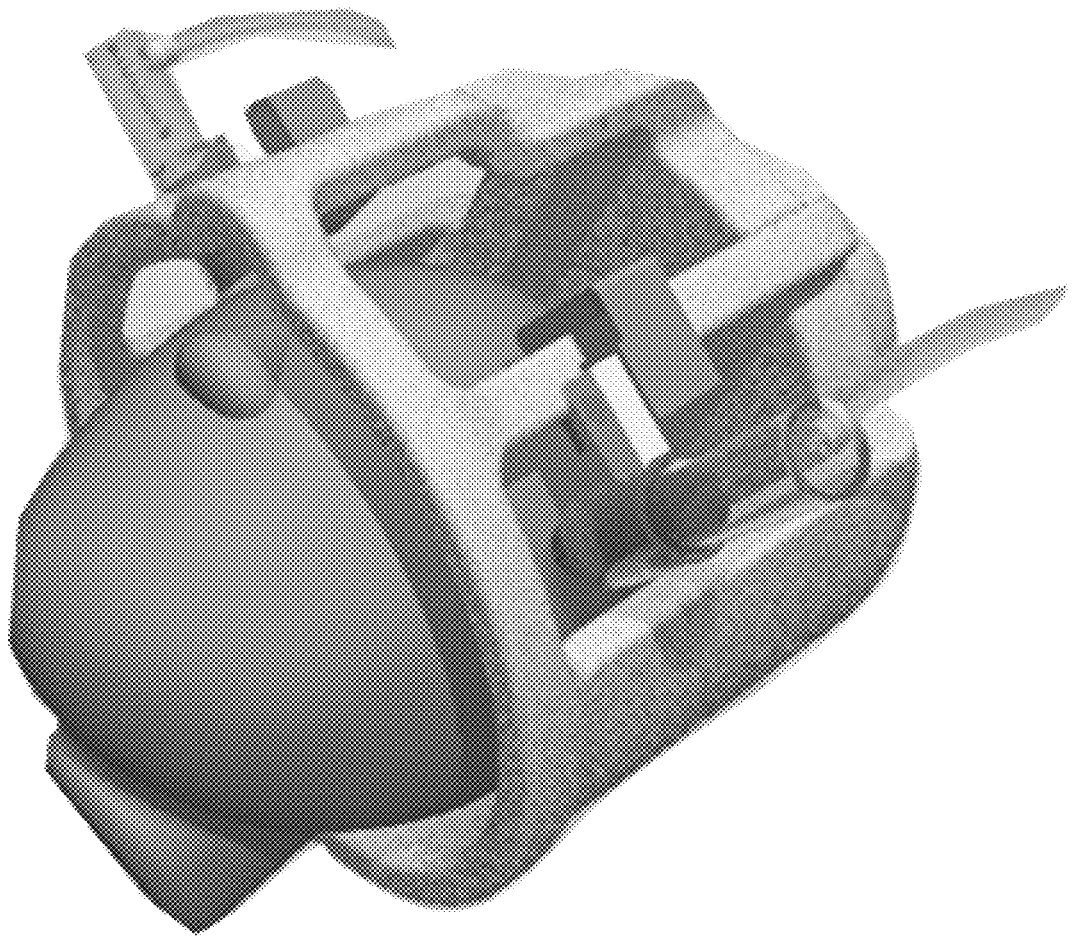
FIG. 2. Schematic of an implementation of the invention, shown situated inside a MRI coil. A magnetic resonance elastography (MRE) actuation device is positioned to vibrate the cheekbone on each side of the subject's head.

The current invention replaces the membrane with, for example, an air-actuated, spring-loaded plastic piston (the material for the piston must be non-metallic to be MRI compatible), as shown in FIG. 1. FIG. 2 shows a schematic of a setup of the device, using two actuators on the two sides of the head and situated inside of a MRI head coil. The device is mounted inside a MRI head coil and pressed up against the subject's cheekbone (technically, the zygoma). The two actuators are operated out of phase (i.e. one "pushes" while the other one "pulls"), creating a side-to-side vibration of the head.

There are at least three advantages to this device, which improve on current practice: 1) it offers comfort and is relatively transparent to the subject (the subject merely feels a slight pressure against the tissue or bone, 2) it produces large amplitude vibrations, while still maintaining subject comfort, and 3) it produces vibrations that are "clean: i.e. free of vibration motion not at the vibration frequency (e.g. higher harmonics).

Figure 3:
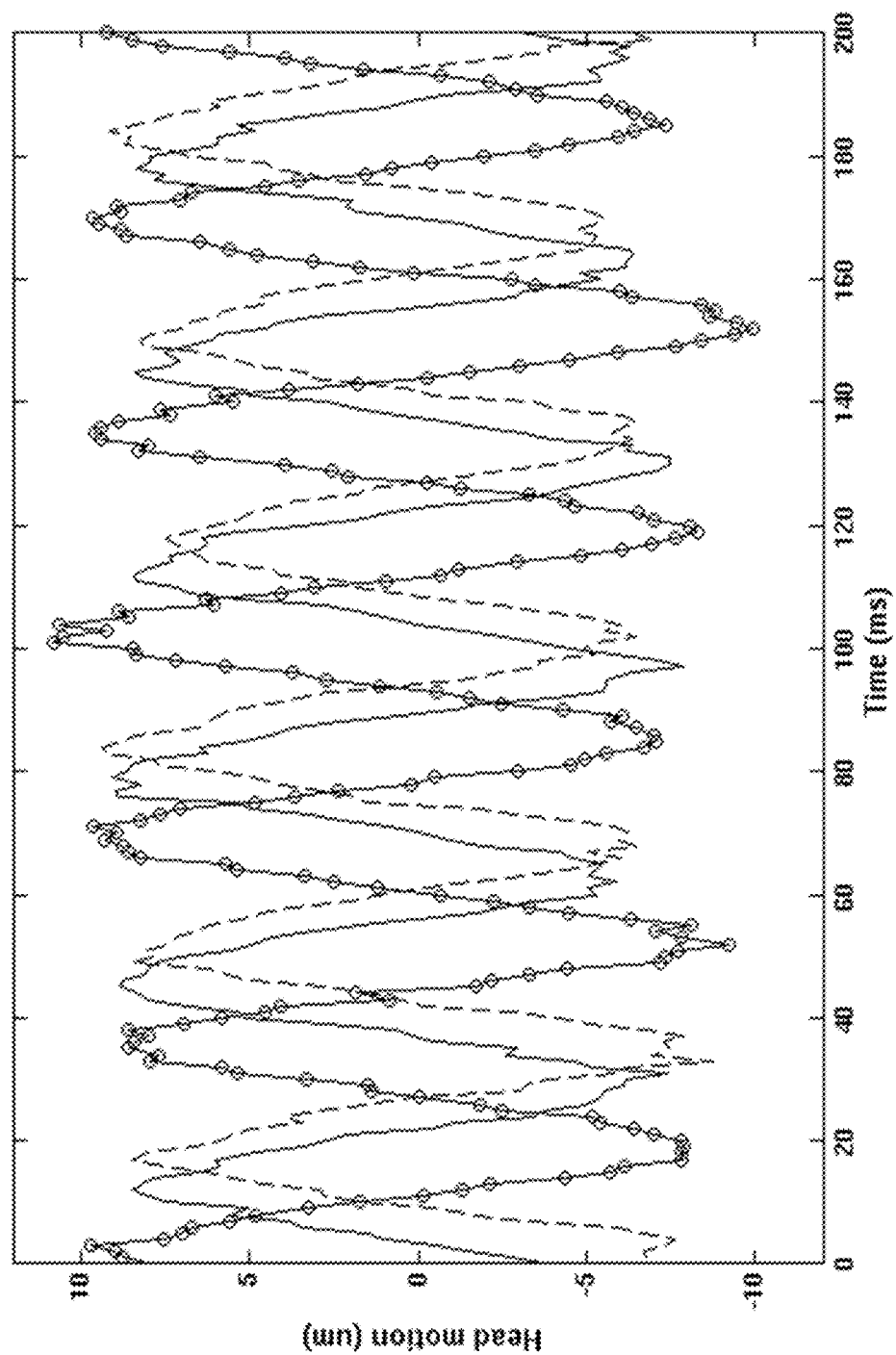
FIG. 3. Demonstration of vibration of sample with the actuator. The three curves show minimal changes in the amplitude of the vibrations with changes in the spring compression. Vibration is at 30 Hz.
Figure 4A:
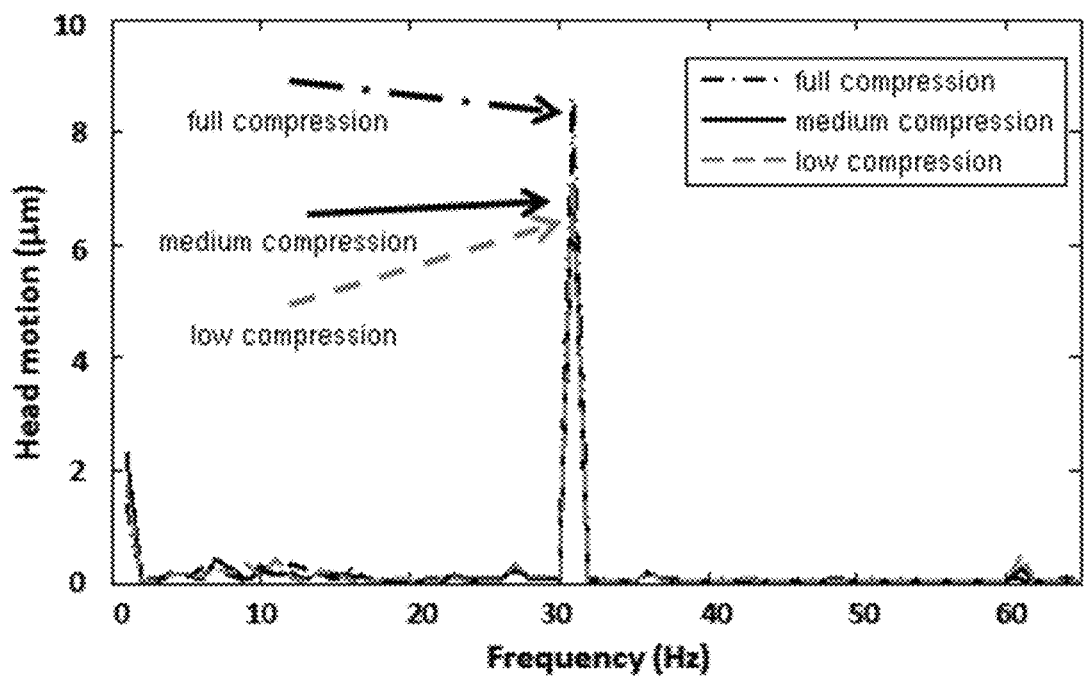
FIG. 4A. Frequency spectrum of vibrations in FIG. 3. While the vibration driver is operated at one frequency, 30 Hz, the head vibrates at 30 Hz as well as at higher frequencies (higher harmonics). Note that with full compression of the springs, the amplitude of the harmonics is dramatically reduced. It is the effect of these higher harmonics that the subject feels and can lead to intolerable operation of the device.
Figure 4B:
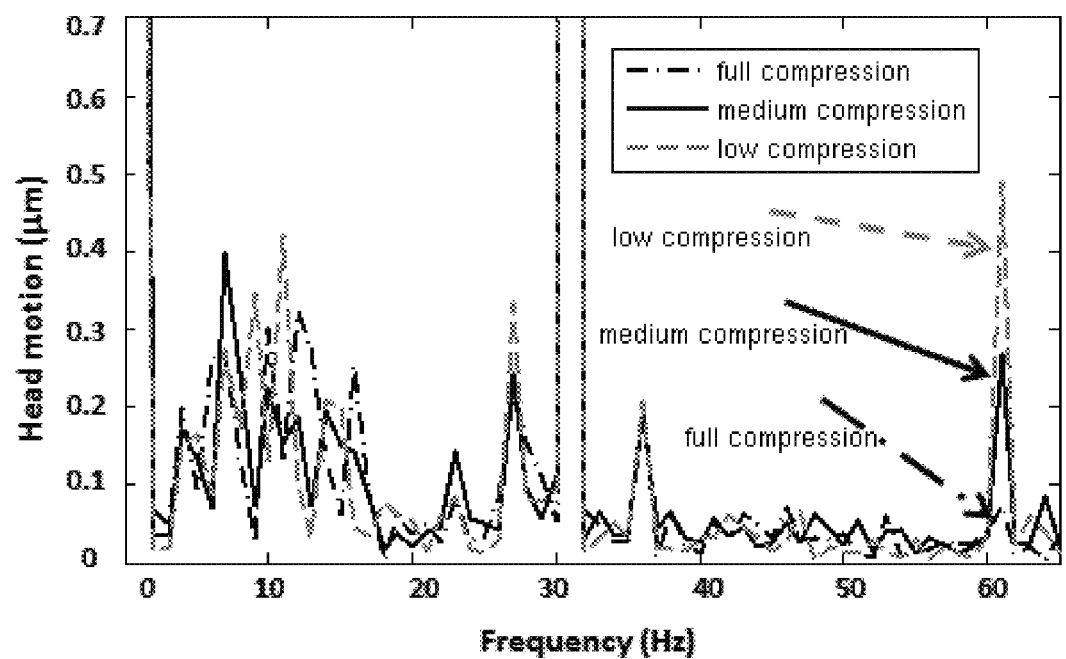
FIG. 4B. Plot from FIG. 4A with expanded vertical axis.

The feeling that the subject has with this device is dependent on the setup of the actuator, as illustrated in FIGS. 3 and 4. With slight compression of the device against the bone, there can be a "jack-hammer" effect. In other words, the piston is not tightly coupled to the bone and the vibration becomes very uncomfortable unless the amplitude of the vibration is turned way down. This is a similar effect to that experienced with a membrane-type actuator—because there cannot be tightly coupling to the skull, there is a jack-hammer affect, necessitating operation at much reduced amplitude to maintain subject comfort (typical shear wave size with this type of actuator is a few microns, compared to 10-20 microns with the new actuator).

However, once the compression of the springs reaches a certain point, the vibration suddenly becomes barely noticeable, feeling like a slight jiggling of the head side to side. This occurs when the actuator is tightly coupled to the bone and the jack-hammer effect is minimized. From a technical standpoint, this occurs because of a minimization of the higher harmonics of the motion, seen in FIG. 4. Note that this minimization of the higher harmonic motion, also will increase the fidelity of the reconstructed shear modulus images, as the amplitude of the vibrations is now at a single frequency and the calculations are more straightforward, as noted above.

Unwanted harmonics can be reduced by adjusting the spring compression.

These figures were created by measuring the acceleration of a subject's head inside the MRI coil, while outside of the MRI, using a standard accelerometer (similar to the one inside an iPhone). The amplitude of the motion is about 120 microns (or about 1/10 of a millimeter), and a subsequent measurement using an MRE sequence inside the MRI revealed that this produced about 50 microns of brain motion.

Figure 5:
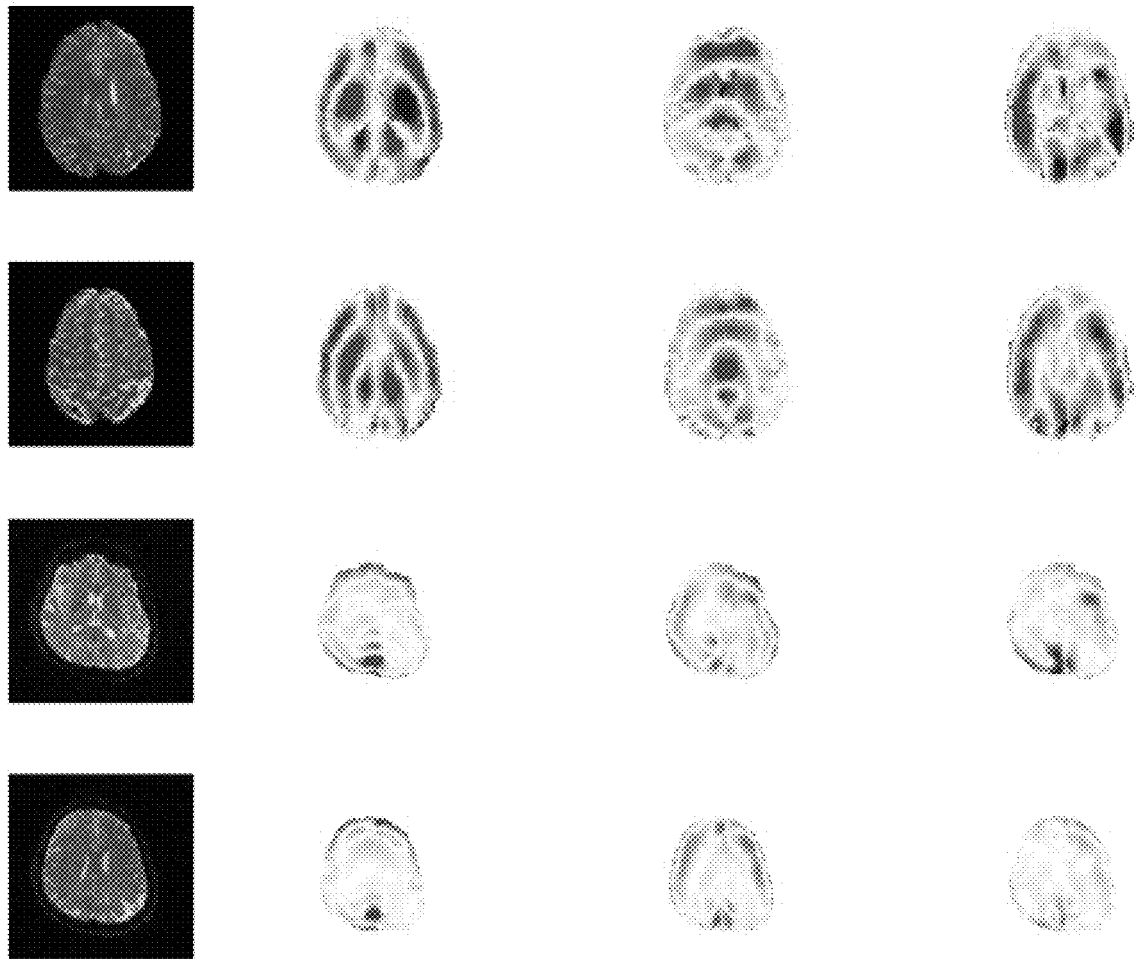
FIG. 5. Total brain motion images at two axial locations with the current actuator (upper two rows), compared to a pillow actuator (lower two rows). The columns represent images for brain motion along the three Cartesian axes.

The amplitude maps created with this actuator were compared with a competing device (comprised of an air-pressure actuated pillow resting below the subject's head) (FIG. 5). Note the increase in the amplitude of the waves as well as the crisp appearance of the waves in the images (which represent shear wave motion in the three Cartesian axes, right-to-left, front-to-back and head-to-foot) produces with the present device (upper two rows) compared to the pillow actuator (bottom two rows).

What is claimed is:

1. A non-metallic magnetic resonance elastography (MRE) actuator comprising:
   a non-metallic body having an open end and a closed end;
   a non-metallic piston disposed within the body, the piston having an end that protrudes from the open end of the body and an opposite end;
   a restorative device that connects the closed end of the body to the opposite end of the piston and that produces a restoring force on the piston when the piston is displaced relative to the body;
   a first non-metallic connector on the body that provides the body with a fluidic connection to a source of pressurized gas that vibrates the piston;
   a non-metallic interface located on the end of the piston that protrudes from the body, where the interface provides a contact area with a subject; and
   a second non-metallic connector on the body that provides mechanical connection with a magnetic resonance imaging (MRI) device.

2. The actuator of claim 1, wherein the restorative device is a spring, foam or rubber restorative device.

3. The actuator of claim 1, wherein any one or more of the body, piston, restorative device, first connector, interface and second connector are made of plastic.

4. The actuator of claim 1, wherein the interface is made of rubber.

5. The actuator of claim 1, wherein the piston is acoustically coupled to a device that provides a vibratory signal to vibrate the piston.

6. The actuator of claim 1, wherein the piston vibrates at a frequency of 20-200 Hz.

7. The actuator of claim 1, wherein the piston vibrates with an amplitude of 10-350 microns, or 10-150 microns, or 100-150 microns.

8. The actuator of claim 1, wherein the actuator is dimensioned and configured for vibrating against bone.

9. The actuator of claim 8, wherein the actuator is dimensioned and configured for imaging the brain or cartilage in the arm or leg.

10. A method of producing a shear wave in a tissue for magnetic resonance elastography (MRE), the method comprising:
    applying a non-metallic interface of a first actuator to skin overlying the tissue to be imaged;
    applying a non-metallic interface of a second actuator to skin overlying the tissue to be imaged, wherein the first actuator is positioned on one side of the tissue to be imaged and the second actuator is positioned on an opposite side of the tissue; and
    vibrating non-metallic pistons of the first and second actuators, wherein the first and second actuators are operated out of phase with each other, wherein the first actuator and the second actuator each comprise:
    a non-metallic body having an open end and a closed end;
    the non-metallic piston disposed within the non-metallic body, the non-metallic piston having an end that protrudes from the open end of the non-metallic body and an opposite end;
    a restorative device that connects the closed end of the non-metallic body to the opposite end of the non-metallic piston and that produces a restoring force on the non-metallic piston when the non-metallic piston is displaced relative to the non-metallic body;
    a first non-metallic connector on the non-metallic body that provides the non-metallic body with a fluidic connection to a source of pressurized gas that vibrates the non-metallic piston;
    the non-metallic interface located on the end of the non-metallic piston that protrudes from the non-metallic body, where the non-metallic interface provides a contact area with a subject; and
    a second non-metallic connector on the non-metallic body that provides mechanical connection with a magnetic resonance imaging (MRI) device.

11. The method of claim 10, wherein the actuator is placed on skin overlying soft tissue.

12. The method of claim 10, wherein the actuator is placed on skin overlying bone, such as cheekbone, skull, pelvic bone or spinal vertebrae.

13. The method of claim 10, wherein one actuator is positioned on skin overlying the left cheekbone and a second actuator is positioned overlying the right cheekbone.

14. The method of claim 10, wherein vibrations are applied to the tissue for 1-15 minutes.

15. The method of claim 10, wherein the method is used for diagnosis and/or prognosis of disease, such as cancer, hydrocephalus, Alzheimer's disease, epilepsy, multiple sclerosis, liver cirrhosis, or liver fibrosis.

\* \* \* \* \*